(12) United States Patent
Tran et al.

(10) Patent No.: US 8,876,892 B2
(45) Date of Patent: Nov. 4, 2014

(54) PROSTHETIC HEART VALVE DELIVERY SYSTEM WITH SPACING

(75) Inventors: Don Tran, Novato, CA (US); Nathan Wiemeyer, Healdsburg, CA (US); Susheel Deshmukh, Santa Rosa, CA (US)

(73) Assignee: Medtronic, Inc., Minneapolis, MN (US)

( * ) Notice: Subject to any disclaimer, the term of this patent is extended or adjusted under 35 U.S.C. 154(b) by 390 days.

(21) Appl. No.: 13/091,949

(22) Filed: Apr. 21, 2011

(65) Prior Publication Data

US 2011/0264200 A1 Oct. 27, 2011

Related U.S. Application Data

(60) Provisional application No. 61/326,279, filed on Apr. 21, 2010.

(51) Int. Cl.
   *A61F 2/24* (2006.01)

(52) U.S. Cl.
   CPC .............. *A61F 2/2436* (2013.01); *A61F 2/2418* (2013.01)
   USPC ...................................................... 623/2.11

(58) Field of Classification Search
   USPC .......... 623/2.1, 2.11, 2.14; 606/108, 200, 198
   See application file for complete search history.

(56) References Cited

U.S. PATENT DOCUMENTS

| | | | |
|---|---|---|---|
| 5,599,305 A | 2/1997 | Hermann et al. | |
| 5,683,451 A | 11/1997 | Lenker et al. | |
| 5,824,041 A | 10/1998 | Lenker et al. | |
| 5,906,619 A | 5/1999 | Olson et al. | |
| 5,957,949 A | 9/1999 | Leonhardt et al. | |
| 7,101,396 B2 | 9/2006 | Artof et al. | |
| 7,105,016 B2 | 9/2006 | Shiu et al. | |
| 7,914,575 B2 * | 3/2011 | Guyenot et al. | 623/2.14 |
| 8,057,539 B2 * | 11/2011 | Ghione et al. | 623/2.11 |
| 8,414,645 B2 * | 4/2013 | Dwork et al. | 623/2.11 |
| 8,512,398 B2 * | 8/2013 | Alkhatib | 623/2.11 |
| 2002/0091434 A1 | 7/2002 | Chambers | |
| 2003/0199963 A1 | 10/2003 | Tower et al. | |
| 2004/0225322 A1 | 11/2004 | Garrison et al. | |
| 2005/0137688 A1 | 6/2005 | Salahieh et al. | |
| 2006/0004439 A1 | 1/2006 | Spenser et al. | |
| 2006/0052867 A1 | 3/2006 | Revuelta et al. | |
| 2006/0229561 A1 | 10/2006 | Huszar | |
| 2006/0259136 A1 | 11/2006 | Nguyen et al. | |
| 2006/0265056 A1 | 11/2006 | Nguyen et al. | |

(Continued)

FOREIGN PATENT DOCUMENTS

| | | |
|---|---|---|
| GB | 2433700 | 7/2007 |
| WO | 2006/076890 | 7/2006 |

(Continued)

*Primary Examiner* — Julian W Woo (57) ABSTRACT

A device for percutaneously deploying a stented prosthetic heart valve includes a distal portion, a spacing collar, and an outer collar. The distal portion provides a coupling structure configured to selectively engage the stented prosthetic heart valve. The spacing collar is located proximal to the distal portion. The spacing collar is transitionable from a loaded state to an activated state. The spacing collar in the loaded state has a radial dimension less than the spacing collar in the activated state. The outer collar is configured to be movable relative to the distal portion and the spacing collar. The outer collar is slidably disposed over the spacing collar to provide the loaded state and is slidably retracted from the spacing collar when in the activated state.

23 Claims, 5 Drawing Sheets

(56) References Cited

U.S. PATENT DOCUMENTS

| | | |
|---|---|---|
| 2007/0005131 A1 | 1/2007 | Taylor |
| 2007/0073387 A1 | 3/2007 | Forster et al. |
| 2007/0088431 A1 | 4/2007 | Bourang et al. |
| 2007/0203503 A1 | 8/2007 | Salahieh et al. |
| 2007/0239266 A1 | 10/2007 | Birdsall |
| 2007/0239269 A1 | 10/2007 | Dolan et al. |
| 2008/0021546 A1 | 1/2008 | Patz et al. |
| 2008/0065011 A1 | 3/2008 | Marchand et al. |
| 2008/0082165 A1 | 4/2008 | Wilson et al. |
| 2008/0140189 A1 | 6/2008 | Nguyen et al. |
| 2008/0147160 A1 | 6/2008 | Ghione et al. |
| 2008/0147181 A1 | 6/2008 | Ghione et al. |
| 2008/0188928 A1 | 8/2008 | Salahieh et al. |
| 2008/0262590 A1 | 10/2008 | Murray |
| 2009/0093876 A1 | 4/2009 | Nitzan et al. |
| 2009/0138079 A1 | 5/2009 | Tuval et al. |
| 2009/0171447 A1 | 7/2009 | Von Segesser et al. |
| 2009/0177275 A1 | 7/2009 | Case |
| 2009/0281619 A1 | 11/2009 | Le et al. |
| 2010/0094411 A1 | 4/2010 | Tuval et al. |
| 2010/0121434 A1 | 5/2010 | Paul et al. |
| 2010/0191326 A1 | 7/2010 | Alkhatib |
| 2010/0249915 A1 | 9/2010 | Zhang |

FOREIGN PATENT DOCUMENTS

| | | |
|---|---|---|
| WO | 2007/071436 | 6/2007 |
| WO | 2008/138584 | 11/2008 |
| WO | 2009/091509 | 7/2009 |
| WO | WO 2011/025945 A1 | 3/2011 |

* cited by examiner

PROSTHETIC HEART VALVE DELIVERY SYSTEM WITH SPACING

CROSS-REFERENCE TO RELATED APPLICATIONS

This application claims priority under 35 U.S.C. §119(e)(1) to U.S. Provisional Patent Application Ser. No. 61/326,279, filed Apr. 21, 2010, entitled "Transcatheter Prosthetic Heart Valve Delivery System with Spacing Feature and Method"; the entire teachings of which are incorporated herein by reference.

BACKGROUND

The present disclosure relates to systems and methods for percutaneous implantation of a heart valve prosthesis. More particularly, the disclosure relates to systems and methods for deploying a transcatheter implantation of a stented prosthetic heart valve at a desired implantation site.

Diseased or otherwise deficient heart valves can be repaired or replaced with an implanted prosthetic heart valve. Conventionally, heart valve replacement surgery is an open-heart procedure conducted under general anesthesia, during which the heart is stopped and blood flow is controlled by a heart-lung bypass machine. Traditional open-heart surgery inflicts significant patient trauma and discomfort. Open-heart surgery also exposes the patient to a number of potential risks. These risks include infection, stroke, renal failure, and adverse effects associated with the use of the heart-lung bypass machine.

Due to the drawbacks of open-heart surgical procedures, there has been an increased interest in minimally invasive and percutaneous replacement of cardiac valves. With these percutaneous transcatheter (or transluminal) techniques, a valve prosthesis is compacted for delivery in a catheter and then advanced, for example, through an opening in the femoral artery and through the descending aorta to the heart. The valve prosthesis is then deployed in the annulus of the valve to be repaired (e.g., the aortic valve annulus). Although transcatheter techniques have attained widespread acceptance with respect to the delivery of conventional stents to restore vessel patency, only mixed results have been realized with percutaneous delivery of a relatively more complex prosthetic heart valve.

Various types and configurations of prosthetic heart valves are available for percutaneous valve procedures and continue to be refined. The actual shape and configuration of any particular prosthetic heart valve is dependent to some extent upon the native shape and size of the valve being repaired (i.e., mitral valve, tricuspid valve, aortic valve, or pulmonary valve). In general, prosthetic heart valve designs attempt to replicate the functions of the valve being replaced and thus will include valve leaflet-like structures. With a bioprostheses construction, the replacement valve may include a valved vein segment that is mounted in some manner within an expandable stent frame to make a valved stent (or "stented prosthetic heart valve"). For many percutaneous delivery and implantation systems, the stent frame of the valved stent is made of a self-expanding material and construction. With these systems, the valved stent is crimped down to a desired size and held in that compressed arrangement within an outer sheath, for example. Retracting the sheath from the valved stent allows the stent to self-expand to a larger diameter, such as when the valved stent is in a desired position within a patient. In other percutaneous implantation systems, the valved stent can be initially provided in an expanded or uncrimped condition, then crimped or compressed on a balloon portion of catheter until it is as close to the diameter of the catheter as possible. Once delivered to the implantation site, the balloon in inflated to deploy the prosthesis. With either of these types of percutaneous stent delivery systems, conventional sewing of the prosthetic heart valve to the patient's native tissue is typically not necessary.

In an attempt to optimize implantation, the stented prosthetic heart valve is accurately located relative to the native annulus immediately prior to full deployment from the catheter. Successful implantation can depend on the prosthetic heart valve being intimately lodge and sealed against the native annulus. If the prosthesis is incorrectly positioned relative to the native annulus, the deployed device can leak and dislodge from the native valve implantation site. As a point of reference, this same concern does not arise in the context of other vascular stents; with these procedures. If the stent is incorrectly deployed, another stent relatively easily can be redeployed in the correct location. If a stented prosthetic heart valve is cantered or moved during retraction of the delivery device, a clinician may have to recapture the heart valve and preposition it or install a new heart valve.

SUMMARY

This summary introduces a selection of concepts in a simplified form that are further described below in the Detailed Description. This summary is not intended to identify key or essential features of the claimed subject matter, and it is not intended to limit the scope of the claimed subject matter.

In one aspect, the disclosure is directed to a device for percutaneously deploying a stented prosthetic heart valve. The device includes a distal portion, a spacing collar, and an outer collar. The distal portion provides a coupling structure configured to selectively engage the stented prosthetic heart valve. The spacing collar is located proximal to the distal portion. The spacing collar is transitionable from a loaded state to an activated state. The spacing collar in the loaded state has a radial dimension less than the spacing collar in the activated state. The outer collar is configured to be movable relative to the distal portion and the spacing collar. The outer collar is slidably disposed over the spacing collar to provide the loaded state and is slidably retracted from the spacing collar when in the activated state.

In another aspect, the disclosure is directed to a delivery system for percutaneously deploying a stented prosthetic heart valve. The delivery system includes an inner shaft assembly extending along an axis of the delivery system. The inner shaft assembly contains a distal portion that provides a coupling structure configured to selectively engage the stented prosthetic heart valve. The delivery system also includes a spacing collar disposed on the axis of the delivery system and proximal to the distal portion. The spacing collar includes circumferentially spaced fingers having a first end coupled to the spacing collar and a second end yieldably urged away from the spacing collar in a radial direction. The fingers are transitionable from a first state in which the second end of the fingers are urged toward the spacing collar to a second state in which the second end of the fingers are expanded away from the spacing collar. Still further, the delivery system includes an outer collar disposed about the axis of the delivery system and slidably disposed over the distal portion including the coupling structure engaged with the stented prosthetic heart valve and the spacing collar including the plurality of fingers. The delivery system includes a loaded configuration where the outer collar is disposed over the spacing collar and the fingers are in the first state. The delivery system also includes an activated configuration where the outer collar is distally retracted from the spacing collar and the fingers are in the second state.

In another aspect, the disclosure is directed to a method of deploying a stented prosthetic heart valve to an implantation site having a vessel wall. For example, the stented prosthetic heart valve is disengaged from a delivery system at a delivery location. A spacing mechanism is activated after the stented prosthetic heart valve is disengaged to space at least a portion of the delivery system away from the vessel wall. The activated delivery system is retracted from the stented prosthetic heart valve.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the disclosure may be practiced. It is to be understood that other embodiments may be utilized and structural or logical changes may be made without departing from the scope of the present disclosure. The following detailed description, therefore, is not to be taken in a limiting sense, and the scope of the present disclosure is defined by the appended claims. It is also to be understood that the features of the various exemplary embodiments described herein may be combined with each other, unless specifically noted otherwise.

The prosthetic heart valve as used in accordance with the various systems, devices, and methods of the present disclosure may include a wide variety of different configurations, such as a bioprosthetic heart valve having tissue leaflets or a synthetic heart valve having a polymeric, metallic, or tissue-engineered leaflets, and can be specifically configured for replacing any heart valve. Thus, the prosthetic heart valve useful with the systems, devices, and methods of the present disclosure can be generally used for replacement of a native aortic, mitral, pulmonic, or tricuspid valves, for use as a venous valve, or to replace a failed bioprosthesis, such as in the area of an aortic valve or mitral valve, for example.

In general terms, the prosthetic heart valves of the present disclosure include a stent or stent frame maintaining a valve structure (tissue or synthetic), with the stent having a normal, expanded arrangement and collapsible to a compressed arrangement for loading within the delivery system. The stent is normally constructed to self-deploy or self-expand when released from the delivery system. For example, the stented prosthetic heart valve useful with the present disclosure can be a prosthetic valve sold under the trade designation CoreValve® available from Medtronic CoreValve, LLC. Other non-limiting examples of transcatheter heart valve prostheses useful with systems and methods of the present disclosure are described in U.S. Publication Nos. 2006/0265056; 2007/0239266; and 2007/0239269, the teachings of each which are incorporated herein by reference. The stents or stent frames are support structures that comprise a number of struts or wire portions arranged relative to each other to provide a desired compressibility and strength to the prosthetic heart valve. In general terms, the stents or stent frames of the present disclosure are generally tubular support structures having an internal area in which valve structure leaflets will be secured. The leaflets can be formed from a verity of materials, such as autologous tissue, xenograph material, or synthetics as are known in the art. The leaflets may be provided as a homogenous, biological valve structure, such as porcine, bovine, or equine valves. Alternatively, the leaflets can be provided independent of one another (e.g., bovine or equine paracardial leaflets) and subsequently assembled to the support structure of the stent frame. In another alternative, the stent frame and leaflets can be fabricated at the same time, such as may be accomplished using high-strength nano-manufactured NiTi films produced at Advanced BioProsthetic Surfaces (ABPS), of San Antonio, Tex. for example. The stent frame support structures are generally configured to accommodate at least two (typically three) leaflets; however, replacement prosthetic heart valves of the types described herein can incorporate more than or less than three leaflets.

Some embodiments of the stent frames can be a series of wires or wire segments arranged such that they are capable of self-transitioning from a collapsed arrangement to a normal, radially expanded arrangement. In some constructions, a number of individual wires comprising the stent frame support structure can be formed of a metal or other material. These wires are arranged in such a way that the stent frame support structure allows for folding or compressing or crimping to the compressed arrangement in which the internal diameter is smaller than the internal diameter when in the natural, expanded arrangement. In the collapsed arrangement, such a stent frame support structure with attached valves can be mounted onto a delivery system. The stent frame support structures are configured so that they can be changed to their natural, expanded arrangement when desired, such as by the relative movement of one or more sheaths relative to a length of the stent frame.

The wires of these stent frame support structures in embodiments of the present disclosure can be formed from a shape memory material such as a nickel titanium alloy (e.g., Nitinol™ available from NDC of Fremont, Calif.). With this material, the support structure is self-expandable from the compressed arrangement to the natural, expanded arrangement, such as by the application of heat, energy, and the like, or by the removal of external forces (e.g., compressive forces). This stent frame support structure can also be compressed and re-expanded multiple times without damaging the structure of the stent frame. In addition, the stent frame support structure of such an embodiment may be laser-cut from a single piece of material or may be assembled from a number of different components. For these types of stent frame structures, one example of a delivery system that can be used includes a catheter with a retractable collar that covers the stent frame until it is to be deployed, at which point the collar can be retracted to allow the stent frame to self-expand. Further details of such embodiments are discussed below.

Figure 1A:
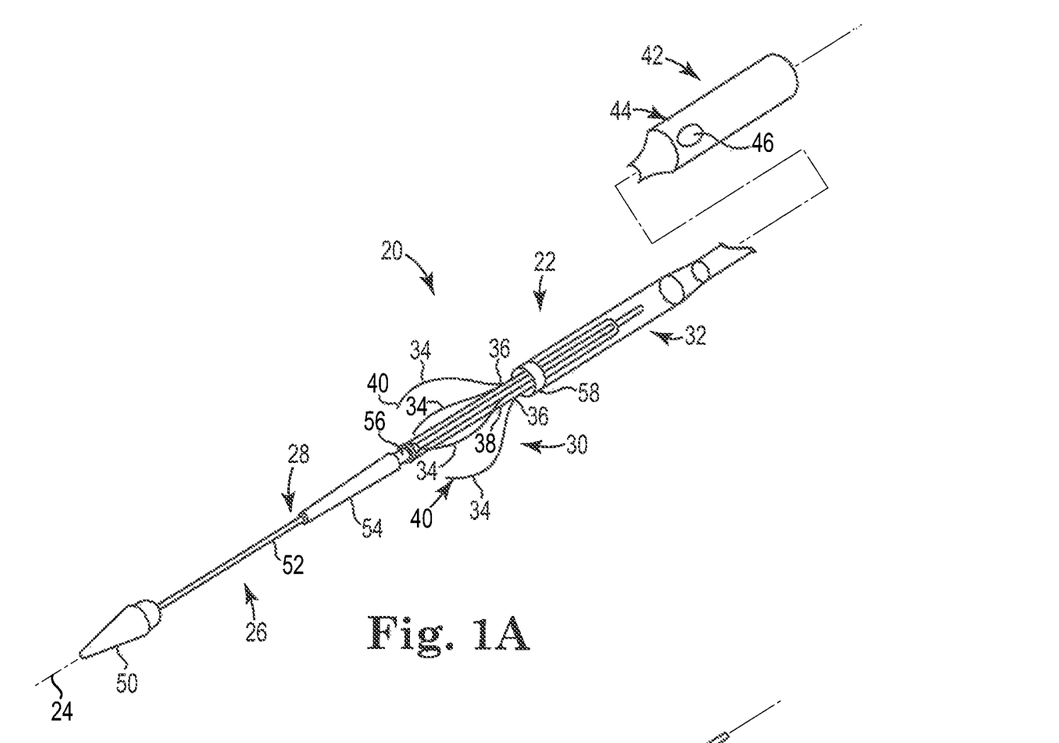
FIG. 1A is a perspective view illustrating a delivery system constructed in accordance with the principles of this disclosure and useful for percutaneously delivering a stented prosthetic heart valve to a heart valve implantation site with the delivery system in an activated configuration.
Figure 1B:
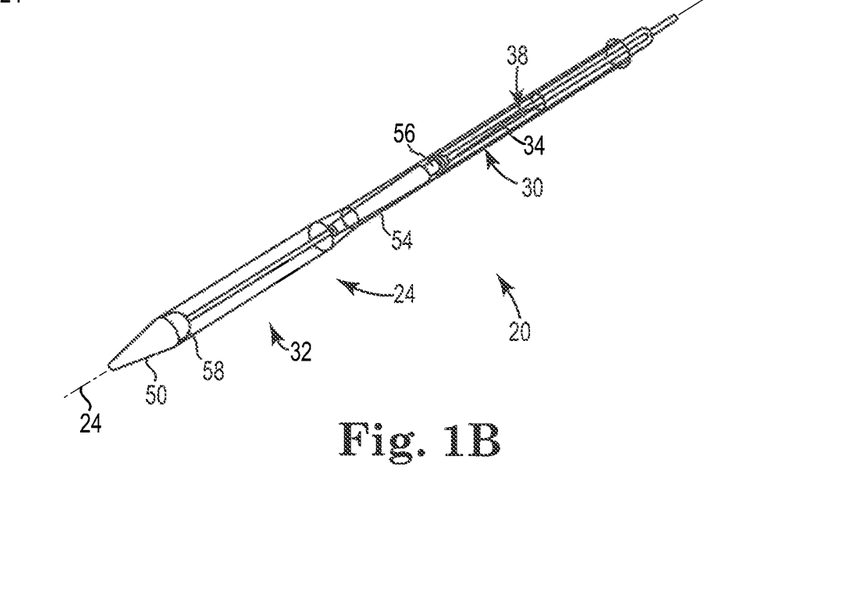
FIG. 1B is a perspective view illustrating the delivery system of FIG. 1A with the delivery system in a loaded configuration.

FIGS. 1A and 1B illustrate a delivery system 20 for percutaneously deploying a stented prosthetic heart valve (not shown) such as with transcatheter and/or transluminal techniques. FIG. 1A illustrates the delivery system 20 in an activated configuration, and FIG. 1B illustrates the delivery system 20 in a loaded configuration. The delivery system 20 can be coupled to other devices to deploy the stented prosthetic heart valve or can deploy the heart valve without other devices such as catheters. The delivery system 20 includes an inner shaft assembly 22 extending along an axis 24 of the delivery system 20. The inner shaft assembly 22 includes a distal portion 26 that provides a coupling structure 28 configured to selectively engage the stented prosthetic heart valve (not shown). The delivery system 20 also includes a spacing collar 30 disposed on the axis 24 of the delivery system 20 and proximal to the distal portion 26. The delivery system 20 includes an outer collar 32 disposed about the axis 24 of the delivery system 20 and slidably disposed over the inner shaft assembly 22 including the coupling structure 28 engaged with the stented prosthetic heart valve (not shown) and the spacing collar 30. In one example, the spacing collar 30 is self-expanding although other configurations are possible.

FIG. 1A also illustrates the spacing collar 30 includes a plurality of circumferentially spaced fingers 34 having a first end 36 coupled to a spacing member 38. The fingers 34 also include a second end 40 yieldably urged away from the spacing member 38 in a radial direction. By yieldably urged away, the fingers 34 are preconfigured to return to a state where the second end 40 is expanded away from the spacing collar member 38 and activated, such as illustrated in FIG. 1A. FIG. 1A also illustrates the delivery system 20 in an activated configuration where the outer collar 32 is proximally retracted from the spacing collar. The fingers 34 are transitionable to another state in which the second end 40 of the fingers 34 are urged toward the spacing member 38 as illustrated in FIG. 1B. FIG. 1B also illustrates the delivery system 20 in a loaded configuration where the outer collar 32 is disposed to cover the spacing collar 30. As used in this disclosure, the spacing collar 30 in the loaded state has a radial dimension less than the spacing collar 30 in the activated state.

The delivery system 20 also includes or can be coupleable to a handle 42 along the axis 24 and disposed at the opposite end of the delivery system 20 from the distal portion 26. The handle 42 generally includes a housing 44 and one or more actuator mechanisms 46 (referenced generally). The housing 44 maintains the actuator mechanism(s) 46, with the handle 42 configured to selectively disengage the stented prosthetic heart valve (not shown) from the distal portion 26 with, for example, the outer collar 32 by facilitating sliding movement relative to the distal portion 26 and the spacing collar 30. The actuator mechanism(s) 46, can also be configured to selectively disengage the stented prosthetic heart valve (not shown) from the distal portion 26 with, for example, the inner shaft assembly 22.

Figure 2A:
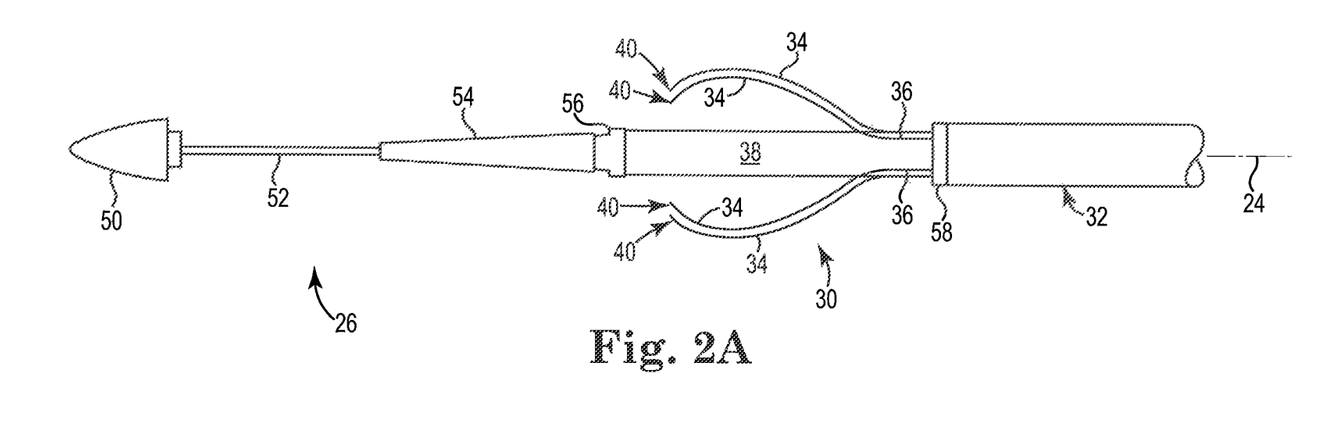
FIG. 2A is a simplified, enlarged view illustrating the delivery system of FIG. 1A in the activated configuration.
Figure 2B:
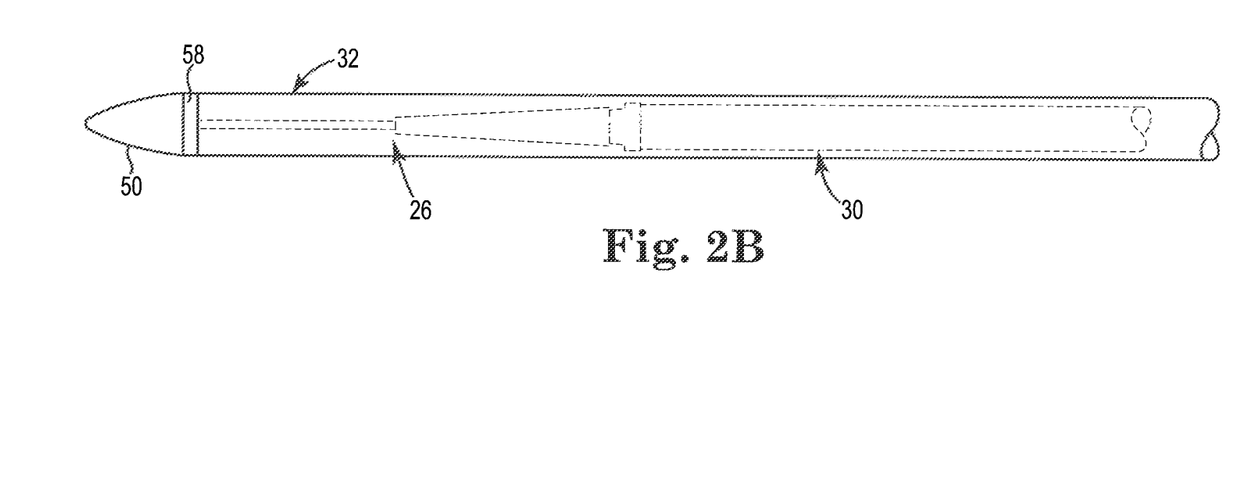
FIG. 2B is a simplified, enlarged view illustrating the delivery system of FIG. 2A in the loaded configuration.

FIGS. 2A and 2B illustrate an example of the delivery system 20 at the distal region including the distal portion 26 and the spacing collar 30. FIG. 2A illustrates the delivery system 20 in the activated configuration corresponding with the illustration in FIG. 1A, and FIG. 2B illustrates the delivery system 20 in the loaded configuration corresponding with the illustration in FIG. 1B. FIG. 2A illustrates the delivery system 20 including the distal portion 26 with the coupling structure 28, the spacing collar 30, and the outer collar 32.

In one example of the delivery system 20, the distal portion 26 includes a tip 50, inner member 52, spacer 54, and spindle 56. The tip 50 is disposed on the distal end of the delivery system 20, and is suited to guide the delivery system 20 through a vascular system to a desired delivery location to deploy the stented prosthetic heart valve. In the example provided, the stented prosthetic heart valve is engaged with the delivery system 20 proximal to the tip 50, around the inner member 52 and distal to the spindle 56. In one example, the stented prosthetic heart valve is coupled or anchored longitudinally to the spindle 56 with an interference fit. The spacer 54 can be used to help properly position the stented prosthetic heart valve against the spindle 56.

FIG. 2B illustrates the outer collar 32 extended to the tip 50 and covering the coupling structure 28, which is selectively engaged with the stented prosthetic heart valve. The outer collar 32 is movable relative to the distal portion 26 and the stented prosthetic heart valve when it engaged in the coupling structure 28. In this loaded configuration, the delivery system 20 can be guided to the desired delivery location to deploy the stented prosthetic heart valve. The outer collar 32 can include a marker band 58, such as a radio-opaque material, or other means of indicating the exact location of the outer collar 32 to a clinician. In the example, the marker band 58 is located at the distal-most end of the tip, which is pulled directly proximate the tip 50 and can be inferentially used to detect the location of the distal most end of the of the stented prosthetic heart valve. A clinician can use the marker band to help detect the desired location of the delivery system 20 and thus determine the preferred location to deploy the stented prosthetic heart valve. Once the preferred location is determined, the outer collar 32 is retracted proximally relative to the distal portion 26, and the stented prosthetic heart valve is deployed once the outer collar 32 is retracted past the spindle 56.

In some circumstances, however, the preferred location to deploy the stented prosthetic heart valve is within a region where the tip 50 is not centered within or ideally spaced-apart from a vascular wall in the location. One such circumstance can occur if the delivery system has passed through a tortuous region of vasculature, such as the aortic arch. If the tip 50 is not properly spaced from the vascular wall, a deployed stented prosthetic heart valve can be cantered against the vascular wall. Also, in cases where the tip 50 is pressed against the vascular wall, the delivery system 20 can become urged against the deployed stented prosthetic heart valve, which can make removal of the delivery system 20 difficult and/or possibly dislodge or move the stented prosthetic heart valve from its desired location.

The delivery system 20 includes the spacing collar 30, which can be used to space the tip 50 away from the vascular wall or to center the tip at the location of deployment. When the outer collar 32 is retracted to reveal the spacing collar 30, the fingers 34 are urged away from the spacing member 38, and the fingers 34 serve to separate the tip 50 from the vascular wall as illustrated in FIG. 2A. When the fingers 34 are circumferentially spaced around the spacing member 38, the fingers 34 can also center the tip 50 at the deployment location. The first end 36 of the fingers 34 are attached to the spacing member 38 in a suitable manner such as heat bonded, molded, with an adhesive, or the like. In one example, the spacing member 38 is constructed from a polymer and the fingers 34 are constructed from a shape memory material such as a nickel titanium alloy (e.g., Nitinol™). In the illustrated example, the fingers 34 are formed to be curved so that the second ends 40 are directed back toward the delivery system 20. Also, in the illustrated example the second ends 40 are distal to the first ends 36 to allow the outer collar 32 to readily extend over the spacing collar 30 and coupling member 26 so that delivery system 20 can be retracted from the patient. The spacing collar 30 is proximal to the spindle 56, and the fingers 34 are also arranged so that the second ends 40 are proximally spaced from the spindle 56, and thus the stented prosthetic heart valve, so as not to interfere with the valve deployment. Although the illustrated examples show four fingers 34, examples are contemplated including more than four or less than four fingers.

Figure 3A:
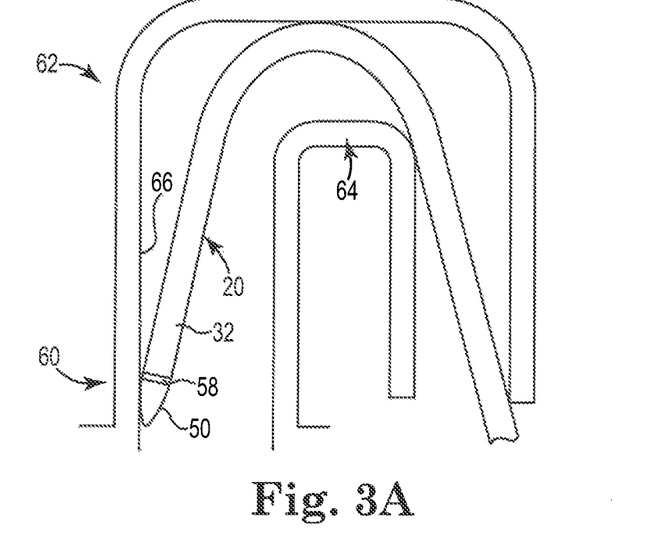
FIGS. 3A-3E are simplified, partial cross-sectional views illustrating use of the delivery system of FIG. 1A in implanting a stented prosthetic heart valve into a patient, including deployment and removal of the delivery system from the patient.

FIGS. 3A-3E illustrate the deployment of the stented prosthetic heart valve. The desired location 60 of the stented prosthetic heart valve in this example is the aorta 62. The tip 50 of the delivery system 20 has been advanced through the patient and is positioned adjacent to the desired location 60, such as adjacent to the outflow side of a valve to be repaired. The delivery system 20 has been traversed through the tortuous path including an aortic arch 64 to reach the desired location 60, and in particular the aortic arch 64 of the aorta 62. In this example, at least a portion of the delivery system 20 (such as the tip 50) rests against the sidewall 66 of the aorta 62 rather than being centered within the aorta 62 and spaced apart from the sidewall 66, as illustrated in FIG. 3A.

Figure 3B:
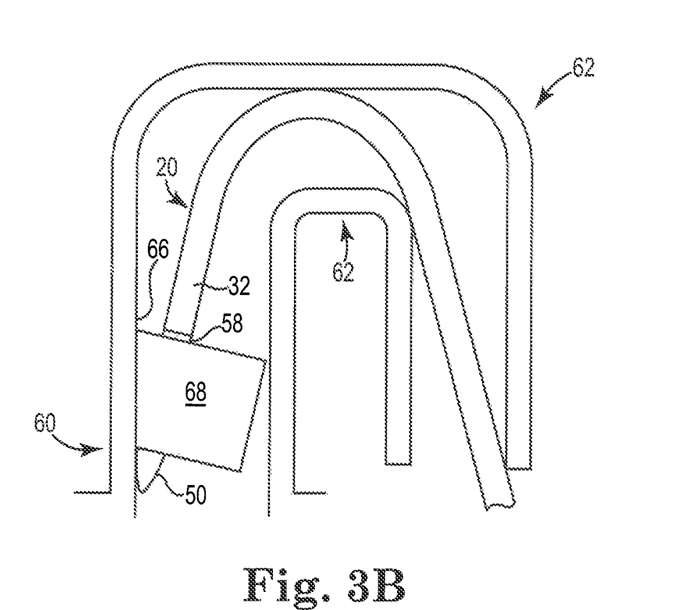

FIG. 3B illustrates the stented prosthetic heart valve, indicated generally at 68, disengaged from the delivery system 20 at a delivery location 60. The outer collar 32 is retracted relative to the distal portion 26 to reveal the stented prosthetic heart valve 68. At this point, the delivery system 20 need not be further advanced into the patient. The stented prosthetic heart valve 68 in the example becomes disengaged from the coupling structure 28 and expands to fit against the aortic sidewall 66. Deployment of the stented prosthetic heart valve 68 can be successful and removal of the delivery system 20 from the desired location 60 can occur without incident when the delivery system 20 is retracted from the desired location 60.

Figure 3C:
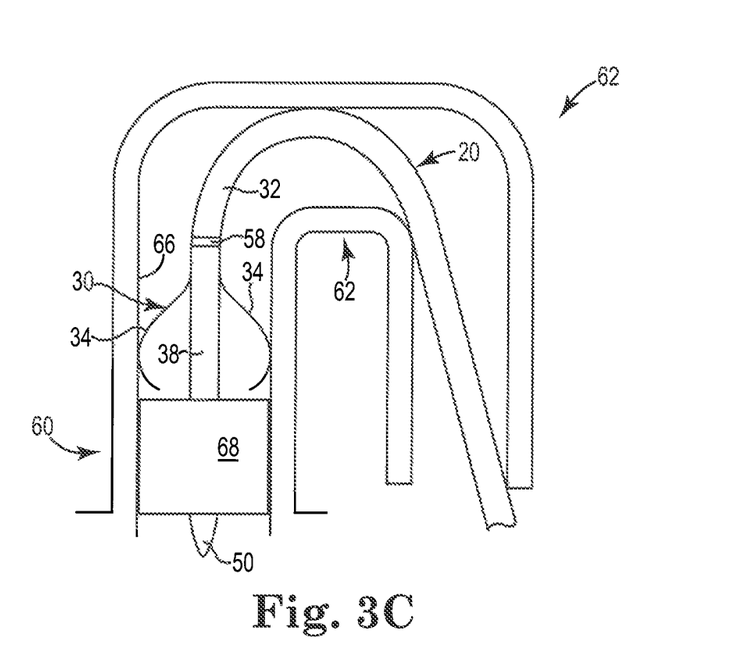

In order to reduce the possibility for the prosthetic valve 68 to canter or for the tip 50 to unintentionally catch against the deployed prosthetic valve 68, i.e., to "hang-up" the deployed valve 68, however, the outer collar 32 is further retracted relative to the spacing collar 30 to activate the fingers 34, as illustrated in FIG. 3C. A spacing mechanism, for example the spacing collar 30, is activated after the stented prosthetic heart valve 68 is disengaged to space at least a portion of the delivery system 20 away from the vessel wall. The fingers 34 serve to space the tip 50 away from the sidewall 66, which can help position the stented prosthetic heart valve 68 so it is not cantered at the desired location 60. Further, in the loaded state, the stent prosthetic heart valve 68 is crimped and anchored longitudinally (along, the axis 24) by an interference fit with the spindle 56 and radially by the outer collar 32 of the delivery system 20. If the delivery system 20 is pressed against the sidewall 66, the stent may not properly disengage itself from the delivery system, which can be called "lock-up." The activated fingers 34 create a space between the stent prosthetic heart valve 68 and the vessel wall 66 to prevent lock-up.

Figure 3D:
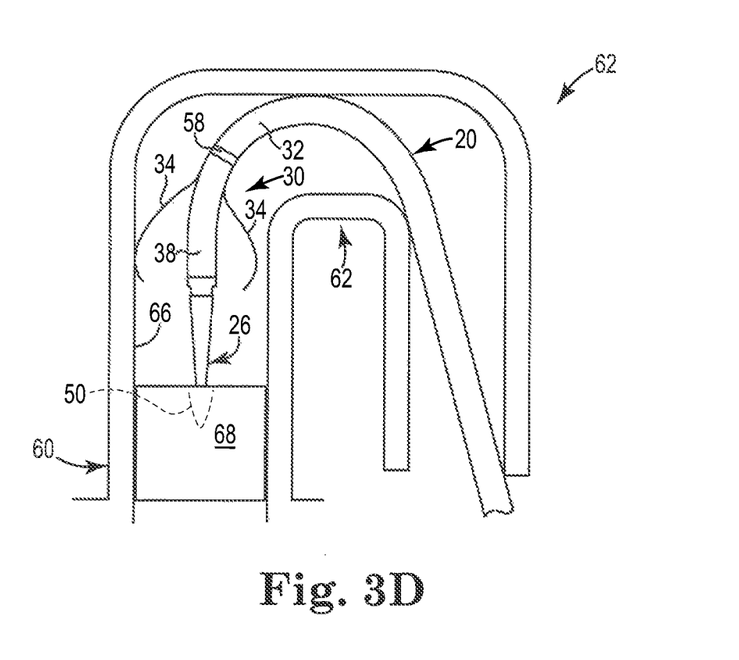
Figure 3E:
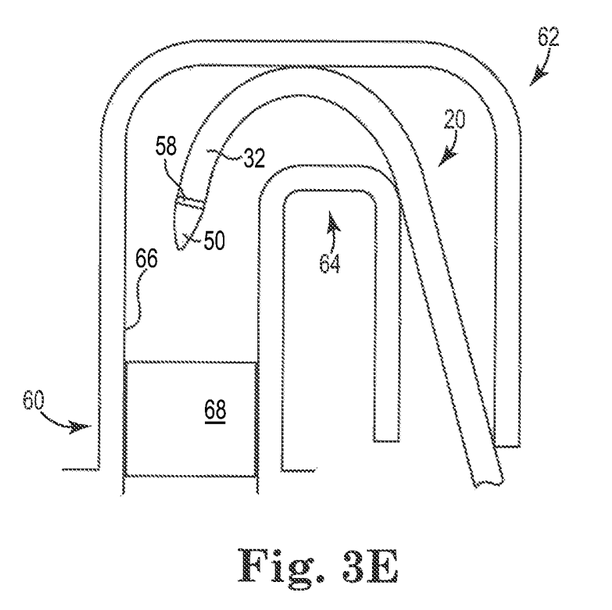

The activated delivery system 20 is then retracted from the stented prosthetic heart valve 68, as illustrated in FIG. 3D. The entire delivery system 20 is retracted from the desired location 60 and the deployed valve 68 with a significantly reduced possibility of hang up with the valve 68. Once the delivery system 20 is retracted from the valve 68, the outer collar 32 can be extended to the tip 50 to cover the spacing collar 30 and the distal portion 26, and the delivery system 20 can be removed from the patient, as illustrated in FIG. 3E.

Although specific embodiments have been illustrated and described herein, it will be appreciated by those of ordinary skill in the art that a variety of alternate and/or equivalent implementations may be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

What is claimed is:

1. A device for percutaneously deploying a stented prosthetic heart valve, the device comprising:
   a distal portion located at the distal end of an axis of the device and configured to selectively engage the stented prosthetic heart valve, wherein the distal portion includes a distal-most tip;
   a spacing collar proximal to and axially spaced apart from the distal portion from the engaged stented prosthetic heart valve, the spacing collar transitionable from a loaded state to an activated state wherein the spacing collar in loaded state has a radial dimension less than the spacing collar in the activated state;
   wherein the spacing collar is configured to be longitudinally spaced-apart along the axis and proximal to the engaged stented prosthetic heart valve while in the loaded state and the activated state, and wherein the spacing collar, distal most tip, and the engaged stented prosthetic heart valve are generally, longitudinally immovable with respect to each other along the axis; a plurality of fingers each having a first end coupled to the spacing collar and a second end yieldably urged away from the spacing collar in a radial direction; and
   an outer collar configured to be movable along the axis relative to the distal portion and the spacing collar such that the outer collar is slidably disposed over the spacing collar to provide the loaded state and is slidably retracted from the spacing collar when in the activated state.

2. The device of claim 1 where in the distal portion includes a tip and a coupling structure, wherein the coupling structure is configured to be selectively engaged with the stented prosthetic heart valve.

3. The device of claim 2 where in the coupling structure includes a spacer and a spindle, wherein the spacer is distally disposed on the device relative to the spindle.

4. The device of claim 3 wherein the spindle is configured to engage the stented prosthetic heart valve.

5. The device of claim 2 wherein the outer collar is slidably movable to be adjacent to the tip.

6. The device of claim 5 wherein the outer collar includes a marker band at a distal most tip of the outer collar.

7. The device of claim 1 and further comprising a handle located on the opposite end of the device from the distal portion.

8. The device of claim 7 wherein the handle includes actuating mechanisms configured to selectively disengage the prosthetic device from the distal portion.

9. The device of claim 7 wherein the handle includes actuating mechanisms configured to facilitate movement of the outer collar relative to the distal portion and the spacing collar.

10. The device of claim 1 wherein the spacing collar is configured to self-expand after the outer collar is retracted from the spacing collar.

11. The device of claim 10 wherein in the spacing collar includes a spacing member.

12. The device of claim 11 wherein the plurality of fingers are circumferentially spaced apart around the spacing member.

13. The device of claim 12 wherein the plurality of fingers includes four fingers.

14. The device of claim 11 wherein the plurality of self-expanding fingers are configured to be disposed proximate to the stented prosthetic heart valve in the loaded state.

15. The device of claim 1, wherein a proximal portion is configured to be operably coupled to a handle.

16. A delivery system for percutaneously deploying a stented prosthetic heart valve, the system comprising:
- an inner shaft assembly extending along an axis of the delivery system, the inner shaft assembly including a distal-most tip and a distal portion providing a coupling structure configured to selectively engage the stented prosthetic heart valve;
- a spacing collar disposed on the axis of the delivery system and proximal to the distal portion and the engaged stented prosthetic heart valve wherein the spacing collar, distal most tip, and the engaged stented prosthetic heart valve are generally, longitudinally immovable with respect to each other along the axis;
- a plurality of circumferentially-spaced fingers each having a first end coupled to the spacing collar and a second end yieldably urged away from the spacing collar in a radial direction;
- wherein the fingers are transitionable from a first state wherein the second end of the fingers are urged toward the spacing collar to a second state wherein the second end of the fingers are expanded away from the spacing collar wherein the fingers are configured to be longitudinally spaced-apart along the axis and proximal to the engaged stented prosthetic heart valve while in the first state and the second state; and
- an outer collar disposed about the axis of the delivery system and slidably disposed over the distal portion including the coupling structure configured to be engaged with the stented prosthetic heart valve and the spacing collar including the plurality of fingers;
- wherein the delivery system includes a loaded configuration wherein the outer collar is disposed over the spacing collar and the fingers are in the first state and an activated configuration wherein the outer collar is distally retracted from the spacing collar and the fingers are in the second state.

17. The delivery system of claim 16 wherein the plurality of circumferentially-spaced fingers are self-expanding.

18. The delivery system of claim 16 wherein the fingers are formed to be curved so that the second ends are radially directed back toward the delivery system.

19. The delivery system of claim 16 wherein the second ends of the fingers are proximal to the stented prosthetic heart valve in the loaded configuration.

20. A method of deploying a stented prosthetic heart valve to an implantation site having a vessel wall, the method comprising:
- selectively engaging the stented prosthetic heart valve on a loaded axial delivery system having a distal portion configured to engage the stented prosthetic heart valve, wherein the distal portion includes a distal-most tip, wherein the delivery system includes a spacing mechanism proximal to and longitudinally spaced-apart from engaged stented prosthetic heart valve on an axis of the delivery system, and wherein the spacing mechanism, distal most tip, and the engaged stented prosthetic heart valve are generally, longitudinally immovable with respect to each other along the axis;
- disengaging the stented prosthetic heart valve from the delivery system at a delivery location wherein at least a portion of the delivery system is urged against the vessel wall;
- activating the spacing mechanism on the delivery system after the stented prosthetic heart valve is disengaged to space at least the portion of the delivery system away from the vessel wall, wherein the spacing mechanism includes a spacing collar and a plurality of circumferentially-spaced fingers each having a first end coupled to the spacing collar and a second end yieldably urged away from the spacing collar in a radial direction; and
- retracting the activated delivery system from the stented prosthetic heart valve.

21. The method of claim 20 and further comprising advancing the delivery system in a loaded configuration with the stented prosthetic heart valve to the implantation site distal to an aortic arch prior to disengaging the stented prosthetic heart valve from the delivery system at the desired location.

22. The method of claim 20 wherein the disengaging the stented prosthetic heart valve from the delivery system includes proximally retracting an outer collar on the delivery system from the stented prosthetic heart valve.

23. The method of claim 20 where the activating the spacing mechanism includes proximally retracting an outer collar on the delivery system from the spacing mechanism.

\* \* \* \* \*